United States Patent
Komine et al.

(10) Patent No.: US 9,995,664 B2
(45) Date of Patent: Jun. 12, 2018

(54) MATERIAL TESTING MACHINE THAT PROPERLY PERFORMS A TENSILE TEST ON A TEST PIECE

(71) Applicants: Shimadzu Corporation, Kyoto-shi (JP); NIHON UNIVERSITY, Tokyo (JP)

(72) Inventors: Noriaki Komine, Kyoto (JP); Susumu Takahashi, Tokyo (JP)

(73) Assignees: Shimadzu Corporation, Nishinokyo-Kuwabaracho, Nakagyo-ku, Kyoto-shi, Kyoto (JP); Nihon University, Kudan-Minami, Chiyoda-ku, Tokyo ( * ) Notice: Subject to any disclaimer, the term of this patent is extended or adjusted under 35 U.S.C. 154(b) by 0 days. days.

(21) Appl. No.: 15/305,129

(22) PCT Filed: May 14, 2014

(86) PCT No.: PCT/JP2014/062854
§ 371 (c)(1),
(2) Date: Oct. 19, 2016

(87) PCT Pub. No.: WO2015/173915
PCT Pub. Date: Nov. 19, 2015

(65) Prior Publication Data
US 2017/0045431 A1 Feb. 16, 2017

(51) Int. Cl.
*G01N 3/08* (2006.01)
*G01N 3/04* (2006.01)

(52) U.S. Cl.
CPC ............. *G01N 3/08* (2013.01); *G01N 3/04* (2013.01); *G01N 2203/0208* (2013.01);
(Continued)

(58) Field of Classification Search
CPC .... G01N 3/08; G01N 3/04; G01N 2203/0208; G01N 2203/0524; G01N 2203/0272; G01N 2203/0282
(Continued)

(56) References Cited

U.S. PATENT DOCUMENTS 6,860,156 B1 * 3/2005 Cavallaro ............... G01N 3/08
73/813
7,712,379 B2 * 5/2010 Abu-Farha ............... G01N 3/04
73/856

(Continued)

FOREIGN PATENT DOCUMENTS

GB  2 101 337 A  1/1983
JP  2012-32218 A  2/2012

*Primary Examiner* — Harshad R Patel
*Assistant Examiner* — Octavia Hollington
(74) *Attorney, Agent, or Firm* — Muir Patent Law, PLLC

(57) ABSTRACT

Seat members 31 are held in a state of being movable with respect to first slide members 21 or second slide members 22 correspondingly. By rotating screws 39 in directions to increase the distances d between surfaces A of the first slide members 21 or the second slide members 22 and surfaces B of the seat members 31, chucks 25 are moved in directions to increase the distance between the chucks to apply pretension to a test piece correspondingly. When backlash in a force transmission system from a support part to the respective chucks 25 is eliminated, a biaxial tensile test is started.

8 Claims, 14 Drawing Sheets

(52) U.S. Cl.
CPC ............... *G01N 2203/0254* (2013.01); *G01N 2203/0272* (2013.01); *G01N 2203/0282* (2013.01)

(58) Field of Classification Search
USPC .......................................................... 73/831
See application file for complete search history.

(56) References Cited

U.S. PATENT DOCUMENTS

| | | | | |
|---|---|---|---|---|
| 8,082,802 | B1* | 12/2011 | Sadegh | G01N 3/08 73/760 |
| 9,423,329 | B2* | 8/2016 | Takeda | G01N 3/08 |
| 9,506,849 | B2* | 11/2016 | Kaneda | G01N 3/04 |
| 2009/0282929 | A1 | 11/2009 | Abu-Farha et al. | |

* cited by examiner

PRIOR ART

MATERIAL TESTING MACHINE THAT PROPERLY PERFORMS A TENSILE TEST ON A TEST PIECE

TECHNICAL FIELD

The present invention relates to a material testing machine that applies tensile forces to a test piece in two mutually intersecting axial directions to perform a test.

BACKGROUND ART

This sort of material test is called a biaxial tensile test, and, for example, performed when measuring the strength of a metal plate. As such a material testing machine, Patent Literature 1 discloses a biaxial tensile testing machine in which each of two rails disposed in mutually orthogonal directions is movably provided with a pair of test piece chuck parts.

FIG. 15 is a perspective view illustrating a biaxial tension mechanism for applying test forces to a test piece 100 in such a conventional material testing machine.

The biaxial tension mechanism in this material testing machine includes a first rail 91 and a second rail 92 that are disposed on the surface of a base plate 90 in mutually orthogonal directions. The first rail 91 is slidably provided with a pair of first moving members 93. The pair of first moving members 93 is guided along the first rail 91, and thereby movable in directions to approach to and separate from each other along the first rail 91. Also, the pair of first moving members 93 is correspondingly provided with chucks 95 for grasping the test piece 100. On the other hand, the second rail 92 is slidably provided with a pair of second moving members 94 (in FIG. 15, only one is illustrated). The pair of second moving members 94 is guided along the second rail 92, and thereby movable in directions to approach and separate from each other along the second rail 92. Also, the pair of second moving members 94 is correspondingly provided with chucks 96 for grasping the test piece 100. The base plate 90 supporting the first rail 91 and the second rail 92 is disposed on a base of the main body of the material testing machine.

Further, the biaxial tension mechanism includes a load member 80 that is connected to a crosshead of the material testing machine and applied with a load by the crosshead. The pair of first moving members 93 is correspondingly connected to the load member 80 through link members 83 including links 81 and links 82. The links 81 included in the link members 83 are swingably connected to the first moving members 93 by shafts 97 correspondingly, and the links 82 included in the link members 83 are swingably connected to the load member 80 by shafts 85 correspondingly. Further, the pair of second moving members 94 is correspondingly connected to the load member 80 through link members 84. One ends of the link members 84 are swingably connected to the second moving members 94 by shafts 98 correspondingly, and the other ends of the link members 84 are swingably connected to the load member 80 by shafts 86 correspondingly.

In the biaxial tension mechanism of the material testing machine, when the load member 80 is pressed in a state where the test piece 100 is grasped by the two pairs of chucks 95 and 96, the pair of first moving members 93 moves in the direction to separate from each other along the first rail 91 by the action of the link members 83 correspondingly, and the pair of second moving members 94 moves in the direction to separate from each other along the second rail 92 by the action of the link members 84 correspondingly. For this reason, the test piece grasped by the two pairs of chucks 95 and 96 is applied with tensile loads in two mutually orthogonal axial directions.

CITATION LIST

Patent Literature

Patent Literature 1: JP-A2012-32218

SUMMARY OF INVENTION

Technical Problem

In such a conventional material testing machine, the gaps existing between the first moving members 93 and the shafts 97 or between the link members 83 and the shafts 97, or the gaps existing between the link members 83 and the shafts 85 or between the load member 80 and the shafts 85 correspondingly cause backlashes in the chucks 95 in a direction of the first rail 92. Similarly, the gaps existing between the second moving members 94 and the shafts 98 or between the link members 84 and the shafts 98, or the gaps existing between the link members 84 and the shafts 86 or between the load member 80 and the shafts 86 correspondingly cause backlashes in the chucks 96 in a direction of the second rail 92. In addition, if the amount of the backlashes in the pair of chucks 95 in the direction of the first rail 91 and the amount of the backlashes in the pair of chucks 96 in the direction of the second rail 92 are different from each other, there occurs a problem of applying inappropriate tensile forces to the test piece 100.

FIG. 16 is a graph illustrating a test result at the time of performing the biaxial tensile test using the conventional material testing machine illustrated in FIG. 15. In FIG. 16, the horizontal axis represents a strain (micro strain) and the vertical axis represents a stress (mega pascal). Also, in this graph, the solid line represents the relationship between the strain and the stress in the first rail 91 direction (X direction) and the dashed line represents the relationship between the strain and the stress in the second rail 92 direction (Y direction).

The test result illustrated in the graph is one obtained when the backlash amount in the pair of chucks 95 in the first rail 91 direction (X direction) was larger than the backlash amount in the pair of chucks 96 in the second rail 92 direction (Y direction). In this case, even when applying test forces in both of the X and Y directions, a stress on the test piece 100 is applied only in the Y direction first, and a positive strain occurs in the test piece 100 in the Y direction. In the case where the positive strain occurs in the test piece 100 in the Y direction as described, in the X direction, a negative strain occurs in the test piece 100. For this reason, as illustrated in FIG. 16, the test piece 100 exhibits unnatural behavior of contracting once and then expanding. As a result, there occurs a problem that the biaxial tensile test cannot be properly performed and thereby the physical properties of the test piece 100 cannot be correctly evaluated.

The present invention is made in order to solve the above-described problem, and intends to provide a material testing machine capable of properly performing a tensile test on a test piece.

Solution to Problem

A first aspect of the present invention is a material testing machine including: a pair of first moving members capable of moving in mutually approaching and separating directions along a first axis by being guided along a guide member; chucks correspondingly connected to the first moving members; a pair of second moving members capable of moving in mutually approaching and separating directions along a second axis intersecting with the first axis by being guided along a guide member; chucks correspondingly connected to the second moving members; a load member to be applied with a load by a load mechanism; four link members that are disposed in states of being swingable with respect to the load member correspondingly around swing shafts disposed in the load member; and connecting mechanisms adapted to connect end parts of the link members on sides opposite to the swing shafts to the first moving members and the second moving members correspondingly, and transmitting the load applied to the load member to the pair of first moving members and the pair of second moving members through the four link members correspondingly to thereby synchronously move the pair of first moving members in the mutually separating directions along the first axis, as well as moving the pair of second moving members in the mutually separating directions along the second axis, and the material testing machine includes pretension mechanisms adapted to apply pretensions to a test piece by in a state where no load is applied to the load member by the load mechanism, moving the pair of chucks correspondingly connected to the pair of first moving members in the mutually separating directions along the first axis as well as moving the pair of chucks correspondingly connected to the pair of second moving members in the mutually separating directions along the second axis.

A second aspect of the present invention is the first aspect of the present invention in which the pretension mechanisms change distances between the end parts of the link members on the sides opposite to the swing shafts and the chucks, and thereby apply the pretensions to the test piece correspondingly.

A third aspect of the present invention is the second aspect of the present invention in which the connecting mechanisms include pins and seating surfaces touching the pins correspondingly; and the pretension mechanisms apply the pretensions to the test piece by changing distances between the pins and the chucks correspondingly.

A fourth aspect of the present invention is the third aspect of the present invention in which the first moving members and the second moving members are configured to include seat members formed with the seating surfaces and slide members holding the seat members correspondingly; and the pretension mechanisms have pressing members that move the seat members with respect to the slide members correspondingly.

A fifth aspect of the present invention is the first aspect of the present invention in which the pretension mechanisms apply the pretensions to the test piece by changing positions of the swing shafts correspondingly.

A sixth aspect of the present invention is the fifth aspect of the present invention in which the swing shafts are pivotally supported by bearing members movable in directions intersecting with longer directions of the link members correspondingly; and the pretension mechanisms comprise pressing members that press the bearing members, and apply the pretensions to the test piece by making the pressing members move the bearing members in the directions intersecting with the longer directions of the link members correspondingly.

A seventh aspect of the present invention is the first aspect of the present invention in which the pretension mechanisms apply the pretensions to the test piece by changing lengths of the link members correspondingly.

An eighth aspect of the present invention is the seventh aspect of the present invention in which the link members correspondingly comprise pairs of link pieces connected through compound screw members each having both ends that are formed with screw parts facing in mutually opposite directions; and the pretension mechanisms apply the pretensions to the test piece by rotating the compound screw members to change distances between the pairs of link pieces correspondingly.

Advantageous Effects of Invention

According to the first to eighth aspects of the present invention, since the pretensions are applied to the test piece in the state where no load is applied to the load member, backlash in any of the chucks can be eliminated and thereby a tensile test can be properly performed on the test piece.

DESCRIPTION OF EMBODIMENTS

Figure 1:
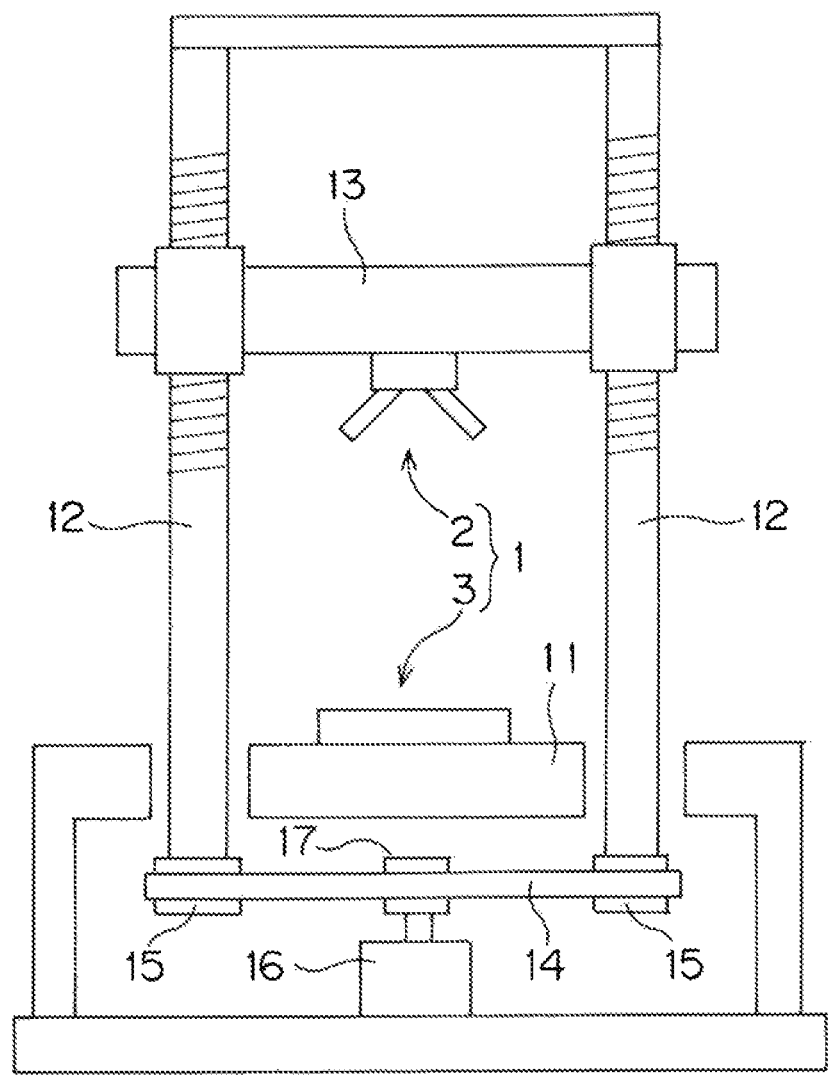
FIG. 1 is a schematic diagram of a material testing machine according to the present invention.

In the following, embodiments of the present invention will be described on the basis of the drawings. FIG. 1 is a schematic diagram of a material testing machine according to the present invention.

The material testing machine includes: a base 11; a pair of left and right screw rods 12 provided upright on the base 11;

and a crosshead 13 that includes nut parts correspondingly screwed with the pair of left and right screw rods 12 and moves up or down with respect to the screw rods 12. The crosshead 13 is provided with an upper unit 2 of the below-described biaxial tension mechanism 1. Further, the base 11 is provided with a lower unit 3 of the below-described biaxial tension mechanism 1.

At the lower end parts of the pair of screw rods 12, synchronous pulleys 15 engaging with a synchronous belt 14 are correspondingly disposed. In addition, the synchronous belt 14 also engages with a synchronous pulley 17 that is rotated by driving of a motor 16. For this reason, the pair of screw rods 12 synchronously rotates by the driving of the motor 16. As a result, the pair of screw rods 12 synchronously rotates, and thereby the cross head 13 moves up or down in an axial direction of the pair of screw rods 12.

Figure 2:
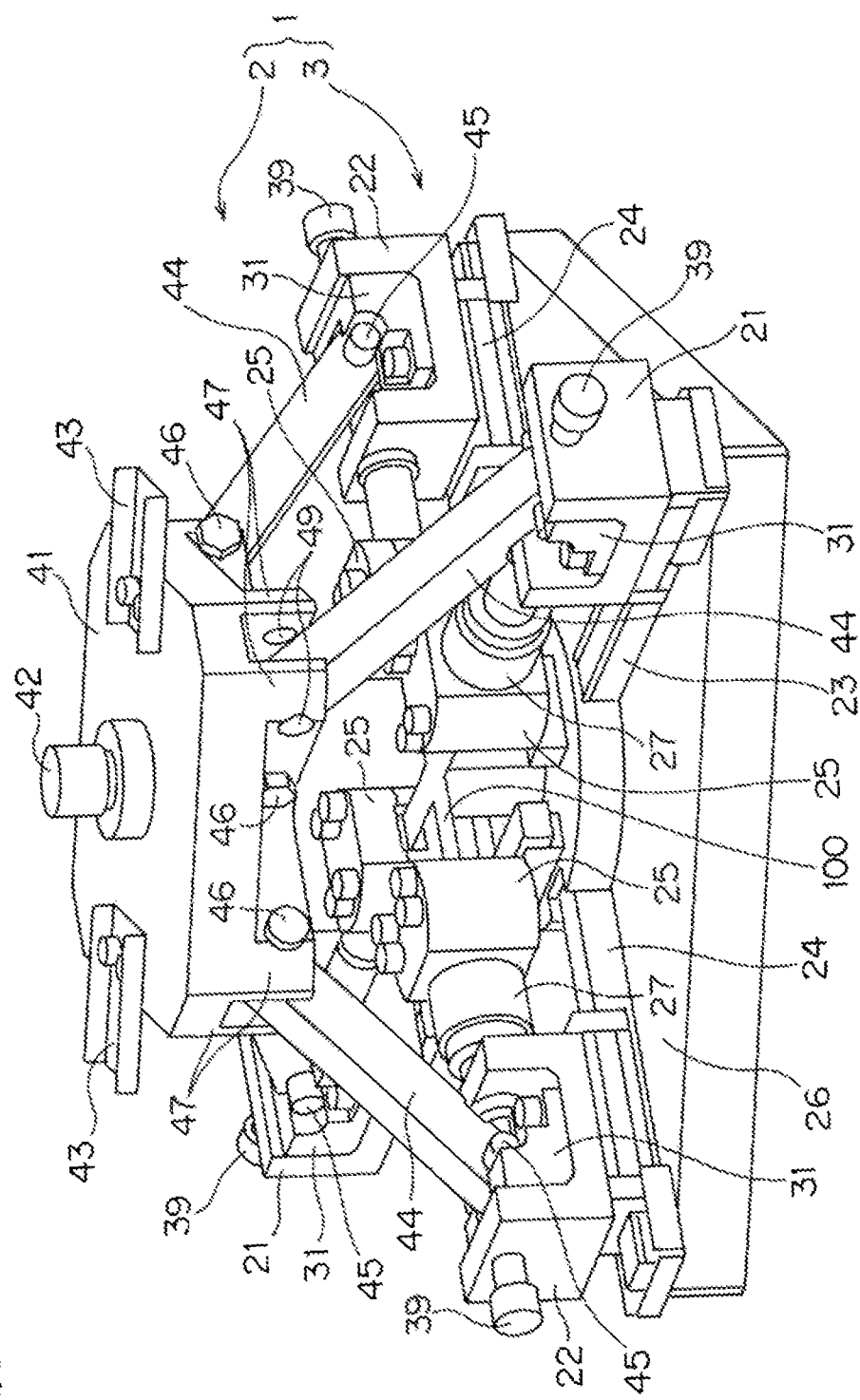
FIG. 2 is a perspective view of a biaxial tension mechanism 1.

FIG. 2 is a perspective view of the above-described biaxial tension mechanism 1. Note that FIG. 2 illustrates a state where the upper and lower units 2 and 3 of the biaxial tension mechanism 1 are connected to each other.

The biaxial tension mechanism 1 includes a first rail 23 and a second rail 24 that are disposed on the surface of a base part 26 in mutually orthogonal directions. The base part 26 supporting the first rail 23 and the second rail 24 is disposed on the base 11 of a main body of the material testing machine illustrated in FIG. 1.

On the first rail 23, a pair of first slide members 21 is slidably disposed. The pair of first slide members 21 is adapted to be movable in directions to approach to and separate from each other along a first axis parallel to the first rail 23 by being guided along the first rail 23. One first slide member 21 of the pair of first slide members 21 is connected to a chuck 25 for grasping a test piece 100 through a load cell 27. On the other hand, the other first slide member 21 of the pair of first slide members 21 is directly connected to a chuck 25. The first slide members 21 correspondingly hold the below-described seat members 31 respectively formed with seating surfaces 29. As will be described later, the positions of the seat members 31 with respect to the first slide members 21 are adjusted by screws 39 correspondingly. Note that the first slide members 21 and the seat members 31 constitute first moving members according to the present invention correspondingly.

On the other hand, on the second rail 24, a pair of second slide members 22 is slidably disposed. The pair of second slide members 22 is adapted to be movable in directions to approach to and separate from each other along a second axis parallel to the second rail 24 by being guided along the second rail 24. One second slide member 22 of the pair of second slide members 22 is connected to a chuck 25 through a load cell 27. On the other hand, the other second slide member 22 of the pair of second slide members 22 is directly connected to a chuck 25. As with the first slide members 21, the second slide members 22 respectively hold seat members 31. As will be described later, the positions of the seat members 31 with respect to the second slide members 22 are also adjusted by screws 39 correspondingly. Note that the second slide members 22 and the seat members 31 constitute second moving members according to the present invention correspondingly.

The first and second rails 23 and 24, first and second slide members 21 and 22, seat members 31, load cells 27, chucks 25, and the like arranged on or above the base part 26 constitute the lower unit 3 of the biaxial tension mechanism 1.

Also, the biaxial tension mechanism 1 includes a support part 41 that is connected to the crosshead 13 of the material testing machine illustrated in FIG. 1 by a connecting member 42. The support part 41 is applied with a load by the crosshead 13 at the time of the below-described biaxial tensile test. The support part 41 is annexed with a pair of lift members 43 used when conveying the biaxial tension mechanism 1 or the upper unit 2 of the biaxial tension mechanism 1 using a forklift or the like. In addition, the support part 41 functions as a load member according to the present invention, which is applied with the load by the crosshead 13 as a load mechanism.

The support part 41 is attached with four link members 44 with each of the four link members 44 held between a pair of joint parts 47 formed integrally with the support part 41. The link members 44 are attached to the pairs of joint parts 47 swingably around swing shafts 46 correspondingly. The support part 41, the four link members 44 attached to the support part 41 through the pairs of joint parts 47 and the swing shafts 46 correspondingly, and the like constitute the upper unit 2 of the biaxial tension mechanism 1.

In addition, among the pairs of joint parts 47 correspondingly supporting the four link members 44, in pairs of joint parts 47 corresponding to the first slide members 21, hole parts 49 different from hole parts through which the swing shafts 46 penetrate are drilled. The hole parts 49 are used when changing the ratio between the test forces applied to the test piece 100 in the mutually orthogonal directions. In that case, among the four link members 44, the two link members 44 swing around the swing shafts 46 fitted into the hole parts 49 correspondingly.

Figure 3:
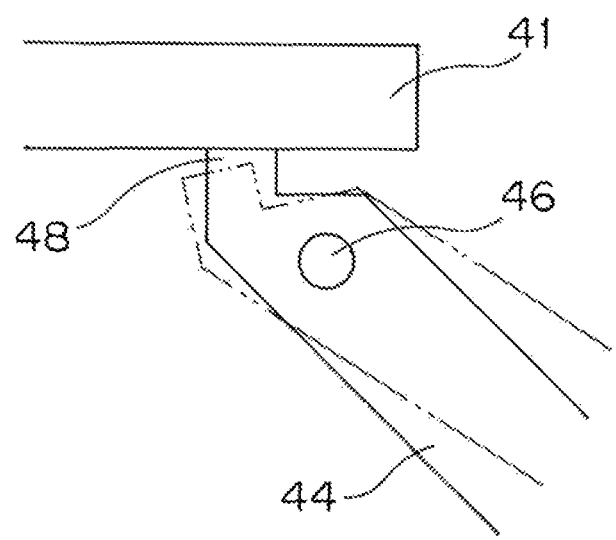
FIG. 3 is an explanatory diagram illustrating an attachment state of a link member 44 to a support part 41.

FIG. 3 is an explanatory diagram illustrating an attachment state of a link member 44 to the support part 41.

As illustrated in FIGS. 2 and 3, the link members 44 are attached to the support part 41 swingably through the pairs of joint parts 47 and the swing shafts 46 correspondingly. In addition, a convex part 48 formed at the upper end of each of the link members 44 touches the lower surface of the support part 41, and thereby the swing of that link member 44 is restricted in a position indicated by a solid line in FIG. 3. For this reason, as will be described later, when separating the upper unit 2 and the lower unit 3 from each other, the respective link members 44 can be prevented from hanging downward.

Referring to FIG. 2 again, near the lower end parts of the respective link members 44, pins 45 are disposed. When connecting the upper unit 2 and the lower unit 3, the pins 45 touch the seating surfaces 29 formed on the seat members 31 correspondingly.

The upper unit 2 of the biaxial tension mechanism 1 is attached to the crosshead 13 of the material testing machine, and the lower unit 3 of the biaxial tension mechanism 1 is annexed to the base 11 of the material testing machine. When performing the biaxial tensile test on the test piece 100, by moving down the crosshead 13 together with the upper unit 2 of the biaxial tension mechanism 1 by the driving of the motor 16 illustrated in FIG. 1, the pins 45 in the upper unit 2 and the seat members 31 in the lower unit 3 are touched correspondingly.

Figure 4:
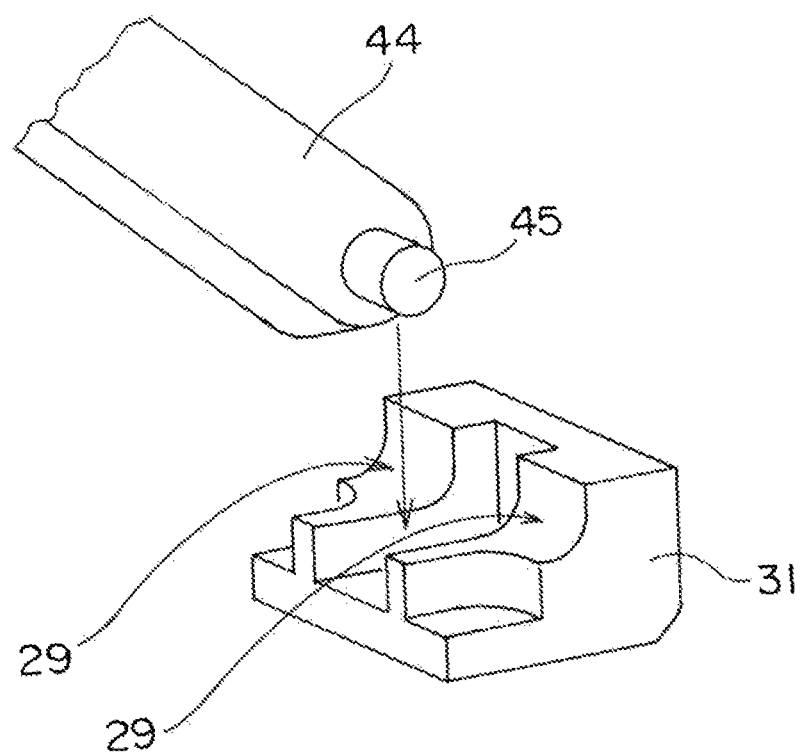
FIG. 4 is a perspective view illustrating a state where a pin 45 and seat members 31 touch each other.
Figure 5:
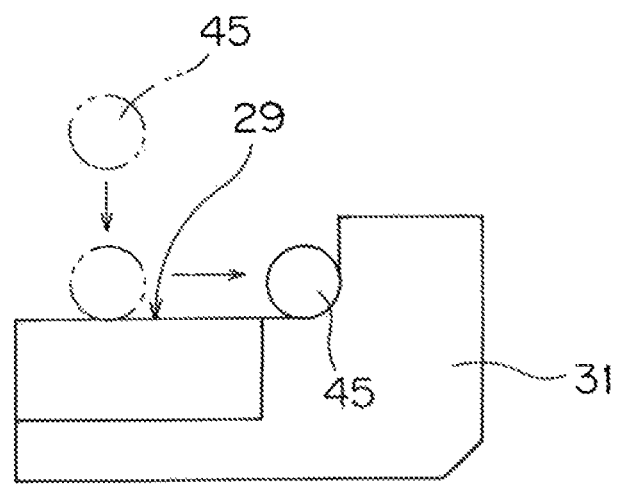
FIG. 5 is a schematic side view of the state where the pin 45 and the seat members 31 touch each other.

FIG. 4 is a perspective view illustrating a state where a pin 45 and a corresponding seat member 31 touch each other, and FIG. 5 is a schematic side view of the state.

The seat members 31 held by the first slide members 21 and the second slide members 22 in the lower unit 3 are formed with the seating surfaces 29 that are to touch the pins 45 disposed on the link members 44 in the upper unit 2 correspondingly. The seating surfaces 29 and the pins 45 have corresponding shapes.

When the crosshead 13 moves down from the state illustrated in FIG. 1, as illustrated in FIGS. 4 and 5, the pins 45 annexed to the link members 44 touch the upper surfaces of the seating surfaces 29 formed on the seat members 31 correspondingly. When from this state, the crosshead 13 further moves down, the pins 45 slide on the seating surfaces 29, and as indicated by a solid line in FIG. 5, touch side surfaces of the seating surfaces 29 correspondingly. At this time, as indicated by a virtual line in FIG. 3, the link members 44 swing around the swing shafts 46 correspondingly.

In addition, when the crosshead 13 further moves down, the pins 45 touching the seating surfaces 29 press the seat members 31 correspondingly. Forces caused by the pressing allow the pair of first slide members 21 to move in the mutually separating directions while being guided along the first rail 23, and the pair of second slid members 22 to move in the mutually separating direction while being guided along the second rail 24. At this time, the outer circumferential surfaces of the pins 45 and the seating surfaces 29 of the seat members 31 slide on each other correspondingly. This allows tensile loads in two mutually orthogonal axial directions to be applied to the test piece 100 grasped by the four chucks 25. In addition, the values of the tensile loads at this time, i.e., the test forces are measured by the pair of load cells 27 correspondingly.

When from this state, the crosshead 13 moves up again together with the upper unit 2 of the biaxial tension mechanism 1, the respective link members 44 swing by their own weights, and as a result, the pins 45 separate from the side surfaces of the searing surfaces 29 correspondingly. Then, when the crosshead 13 further moves up, the pins 45 separate from the seating surfaces 29 as the link members 44 moves up because regions of the seating surfaces 29 formed on the seat members 31 in directions other than directions in which the seating surfaces 29 touch the pins 45 and are applied with the loads are open parts correspondingly.

Figure 6:
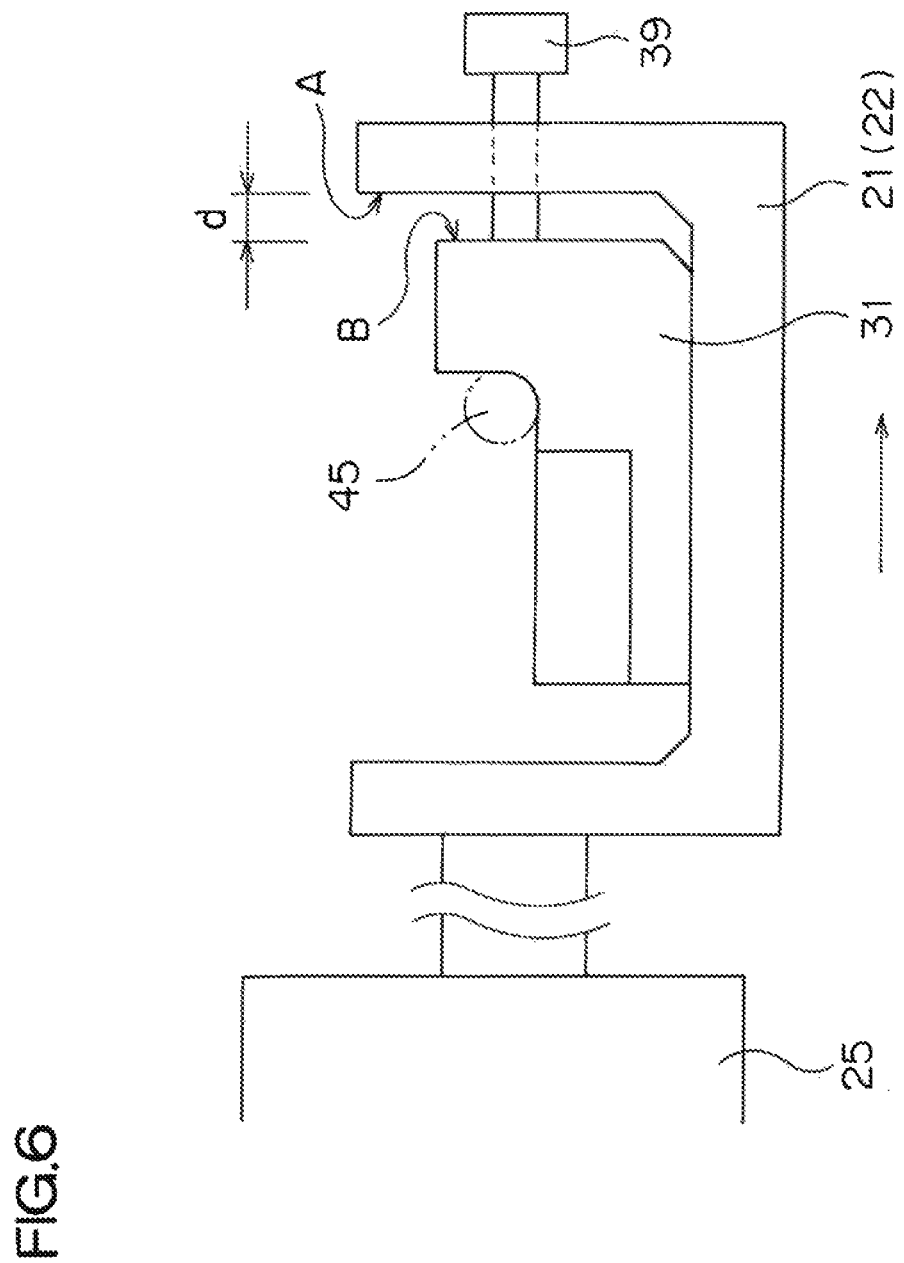
FIG. 6 is a schematic side view illustrating a mechanism adapted to move a seat member 31 with respect to a first or second slide member 21 or 22.

FIG. 6 is a schematic side view illustrating a pretension mechanism according to a first embodiment adapted to move a seat member 31 with respect to a first or second slide member 21 or 22.

As illustrated in FIG. 6, the seat member 31 is held in a state of being movable with respect to the first slide member 21 or the second slide member 22. Also, the position of the seat member 31 with respect to the first slide member 21 or the second slide member 22 is adjusted by rotating a screw 39 disposed in the first slide member 21 or the second slide member 22. When doing this, the seat member 31 is restricted from moving because as described above, seating surfaces 29 of the seat member 31 touch a pin 45. For this reason, when rotating the screw 39 in a direction to increase the distance d between a surface A of the first slide member 21 or the second slide member 22 and a surface B of the seat member 31, the first slide member 21 or the second slide member 22 moves in a direction to separate from the pin 45 (a direction indicated by an arrow in FIG. 6).

Note that one first slide member 21 of the pair of first slide members 21 is connected to the chuck 25 through the load cell 27, and the other first slide member 21 is directly connected to the chuck 25, correspondingly. For this reason, when the first slide members 21 move in the direction indicated by the arrow illustrated in FIG. 6 along the first rail 23, the pair of chucks 25 move in the mutually separating directions. At this time, the test piece 100 grasped by the chucks 25 is subjected to tension along the first axis parallel to the first rail 23. Similarly, one slide part 22 of the pair of second slide parts 22 is connected to the chuck 25 through the load cell 27, and the other second slide member 22 is directly connected to the chuck 25, correspondingly. For this reason, when the second slide members 22 move in the direction indicated by the arrow illustrated in FIG. 6 along the second rail 24, the pair of chucks 25 moves in the mutually separating direction. At this time, the test piece 100 grasped by the chucks 25 is subjected to tension along the second axis parallel to the second rail 24.

Next, actions taken when performing the biaxial tensile test on the test piece 100 using the biaxial tension mechanism 1 will be described.

At the start of the test, the crosshead 13 illustrated in FIG. 1 is arranged above. Also, as described above, the upper unit 2 of the biaxial tension mechanism 1 is attached to the crosshead 13 of the material testing machine, and the lower unit 3 of the biaxial tension mechanism 1 is annexed to the base 11 of the material testing machine. In this state, on the lower unit 3 of the biaxial tension mechanism 1, the upper unit 2 is not arranged, and therefore the upper parts of the respective chucks 25 in the lower unit 3 are opened. As a result, the test piece 100 can be easily attached on the chucks 25. Even if the use of a tool such as a wrench is required when attaching the test piece 100, work using the tool can be easily done. Note that in this state, in the upper unit 2 of the biaxial tension mechanism 1, as illustrated in FIG. 3, the convex parts 48 formed at the upper ends of the link members 44 touch the lower surface of the support part 3, and thereby the link members 44 are arranged in the positions each indicated by the solid line in FIG. 3, correspondingly.

When the attachment of the test piece 100 on the respective chucks 25 has been completed and the biaxial tensile test is performed on the test piece 100, the crosshead 13 is moved down together with the upper unit 2 of the biaxial tension mechanism 1 by the driving of the motor 16 illustrated in FIG. 1, and thereby the pins 45 in the upper unit 2 are touched to the seat members 31 in the lower unit 3 correspondingly. At this point of time, the downward movement of the crosshead 13 is once stopped.

Figure 16:
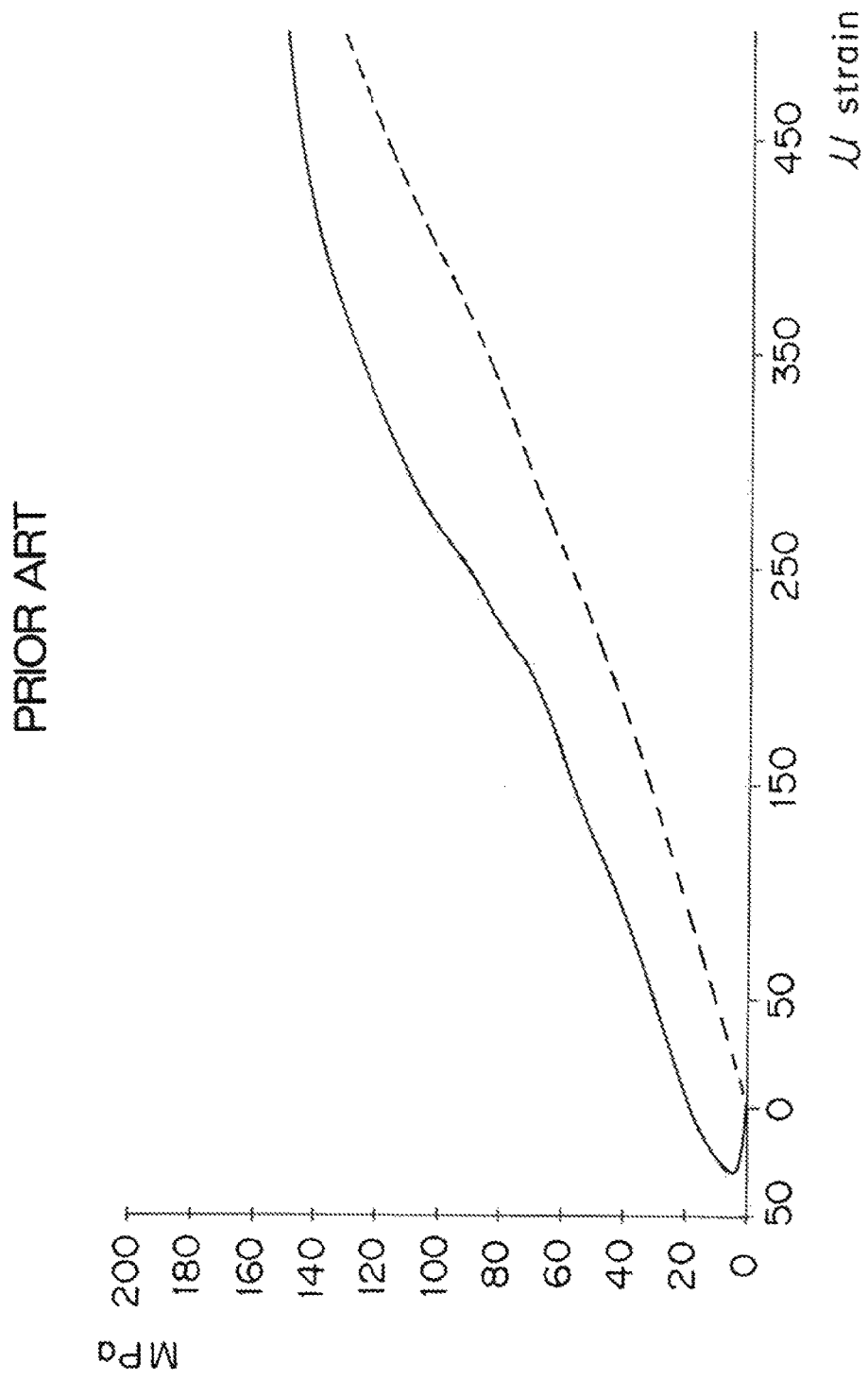
FIG. 16 is a graph illustrating a test result at the time of performing a biaxial tensile test using the conventional material testing machine.

When from this state, further moving down the upper unit 2, tensile forces act on the test piece 100 in the two axial directions. However, if backlash occurs in a power transmission system from the support part 41 to the respective chucks 25, as illustrated in FIG. 16, the test piece 100 may exhibit the unnatural behavior of contracting once in the X direction and then expanding. As a result, there occurs a problem that the biaxial tensile test cannot be properly performed, and thereby the physical properties of the test piece 100 cannot be correctly evaluated.

For this reason, as described above, by rotating the screws 39 illustrated in FIG. 6 in directions to increase the distances d between the surfaces A of the first slide members 21 or the second slide members 22 and the surfaces B of the seat members 31, the chucks 25 are moved in directions to increase the distances between the pairs of opposite chucks 25 and thereby pretensions are applied to the test piece 100, correspondingly. When doing this, since the pretensions are applied to the test piece 100 in the two mutually orthogonal directions, in order to prevent uneven pretensions from being applied to the test piece 100, by rotating the four screws 39 of the pair of first slide members 21 and the pair of second slide members 22, the positions of the four chucks 25 are adjusted. When making the adjustment, it may be configured to refer to signals of the load cells 27. In addition, it may be configured to use, in place of the screws 39 as pressing members adapted to press the seat members 31 in FIG. 6, wedges as the pressing members, and thereby increase the distances d between the surfaces A and the surfaces B to apply the pretensions correspondingly. Note that the pretensions here refer to initial tensile loads applied to the test piece 100 before performing the biaxial tensile test.

After the backlash in the force transmission system from the support part 41 to the respective chucks 25 has been eliminated, the biaxial tensile test is started. When doing this, the crosshead 13 is further moved down to press the seat members 31 with the pins 45 touching the seating surfaces 29 correspondingly. The forces caused by the pressing allow the pair of first slide members 21 to move in the mutually separating directions while being guided along the first rail 23, and the pair of second slide members 22 to move in the mutually separating direction while being guided along the second rail 24. This allows the tensile loads in the two mutually orthogonal axial directions to be applied to the test piece 100 grasped by the four chucks 25. In addition, the values of the tensile loads at this time, i.e., the test forces are measured by the pair of load cells 27 correspondingly.

Figure 7:
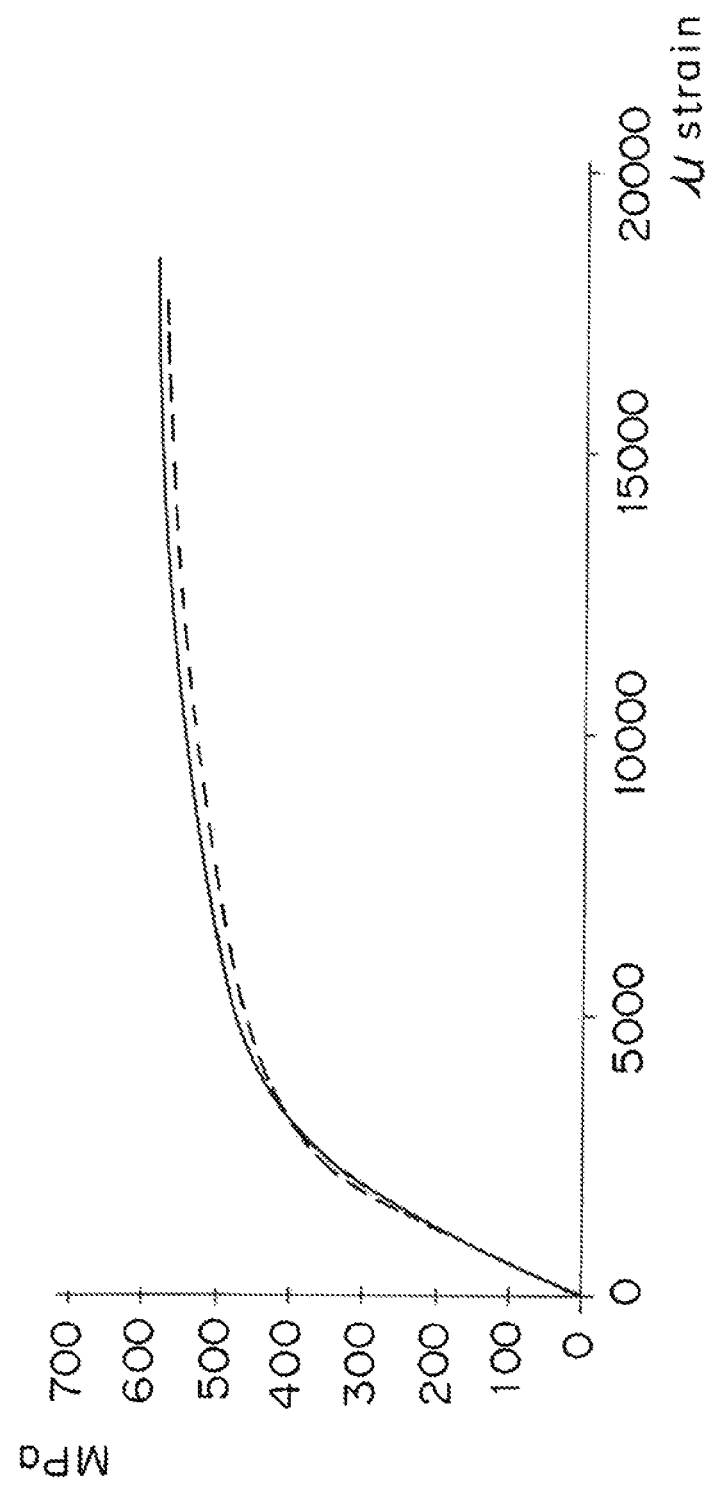
FIG. 7 is a graph illustrating a test result at the time of performing a biaxial tensile test with using the material testing machine according to the present invention.

FIG. 7 is a graph illustrating a test result at the time of performing the biaxial tensile test using the material testing machine according to the present invention. In FIG. 7, the horizontal axis represents a strain (micro strain), and the vertical axis represents a stress (mega pascal). Also, in the graph, the solid line represents the relationship between the strain and the stress in the first rail 91 direction (X direction), and the dashed line represents the relationship between the strain and the stress in the second rail 92 direction (Y direction).

As illustrated in the graph, in both of the X and Y directions, the strains increase as the stresses applied to the test piece 100 are increased. From this, it can be understood that during the material test, the unnatural behavior of the test piece 100 as illustrated in FIG. 16 is eliminated, and the biaxial tensile test of the test piece 100 is properly performed.

After the biaxial tensile test has been finished, the crosshead 13 is moved up again together with the upper unit 2 of the biaxial tension mechanism 1. When the upper unit 2 moves up, the respective link members 44 swing by their own weights, and as a result, the pins 45 separate from the side surfaces of the seating surfaces 29 correspondingly. Then, when the crosshead 13 further moves up, the pins 45 separate from the seating surfaces 29 as the link members 44 move up because the regions of the seating surfaces 29 formed on the seat members 31 in directions other than directions in which the seating surfaces 29 touch the pins 45 and are applied with the loads are open parts, correspondingly. At this time, as indicated by the solid line in FIG. 3, the swings of the link members 44 are stopped when the convex parts 48 formed at the upper ends of the link members 44 reach the positions to touch the lower surface of the support part 41 correspondingly. For this reason, the swings of the link members 44 can be kept within a certain range to prevent the link members 44 from hanging down.

When the crosshead 13 is arranged in the upper position again as illustrated in FIG. 1, the test piece 100 is removed from the chucks 25. At this time as well, since the upper parts of the respective chucks 25 in the lower unit 3 of the biaxial tension mechanism 1 are opened, the test piece 100 can be easily removed from the chucks 25.

The above-described embodiment employs a pretension mechanism adapted to apply the pretensions to the test piece 100 by relatively moving the first and second slide members 21 and 22 and the seat members 31 using the pins 45 disposed on the link members 44, the seat members 31 including the seating surfaces 29 to touch the pins 45, and the first and second slide members 21 and 22 and thereby changing the distances between the pins 45 and the chucks 25, correspondingly. However, as the pretension mechanism adapted to change the distances between the pins 45 and the chucks 25 correspondingly, a mechanism having another configuration can also be employed.

Figure 8:
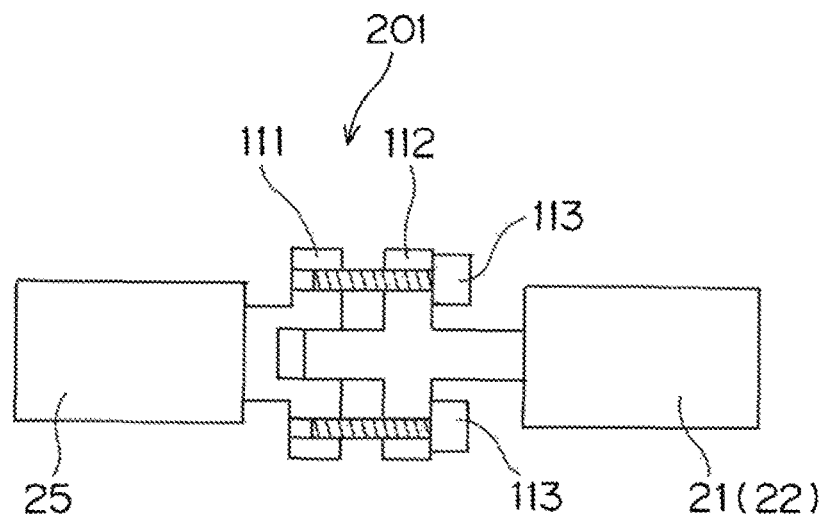
FIG. 8 is a schematic diagram of a pretension mechanism 201 according to a second embodiment.

FIG. 8 is a schematic diagram of a pretension mechanism 201 according to a second embodiment. Note that in the diagram, a first slide member 21 or a second slide member 22 and a chuck 25 are directly connected to each other by the pretension mechanism 201; however, when disposing a load cell 27, the load cell 27 is disposed between the first slide member 21 or the second slide member 22 and the pretension mechanism 201 or between the chuck 25 and the pretension mechanism 201.

The pretension mechanism 201 is configured to connect a connecting member 112, which is annexed to the first slide member 21 or the second slide member 22 and cross-shaped in a side view, and a connecting member 111, which is annexed to the chuck 25 and has a concave part, by a pair of screws 113. The connecting member 111 is formed with the concave part into which the fore end of the connecting member 112 is inserted. In the pretension mechanism 201, by rotating the pair of screws 113 to change the distance between a pin 25 and the chuck 25 connected to the first slide member 21 or the second slide member 22, pretension can be applied to a test piece 100.

Figure 9:
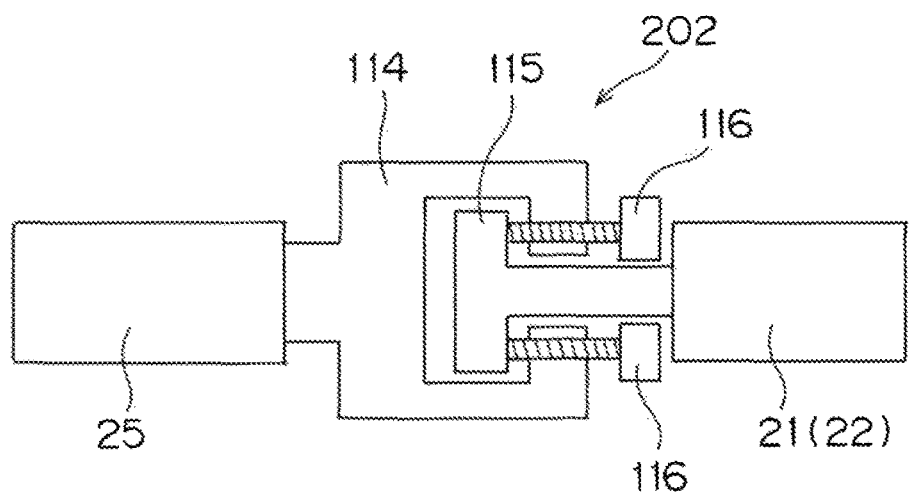
FIG. 9 is a schematic diagram of a pretension mechanism 202 according to a third embodiment.

FIG. 9 is a schematic diagram of a pretension mechanism 202 according to a third embodiment. Note that in the diagram, a first slide member 21 or a second slide member 22 and a chuck 25 are directly connected to each other by the pretension mechanism 202; however, when disposing a load cell 27, the load cell 27 is disposed between the first slide member 21 or the second slide member 22 and the pretension mechanism 202 or between the chuck 25 and the pretension mechanism 202.

The pretension mechanism 202 is configured to connect a connecting member 115, which is annexed to the first slide member 21 or the second slide member 22 and T-shaped, and a connecting member 114, which is annexed to the chuck 25 and has a shape surrounding the connecting member 115, by a pair of screws 116. In the pretension mechanism 202, by rotating the pair of screws 116 to change the distance between a pin 25 and the chuck 25 connected to the first slide member 21 or the second slide member 22, pretension can be applied to a test piece 100.

Figure 10:
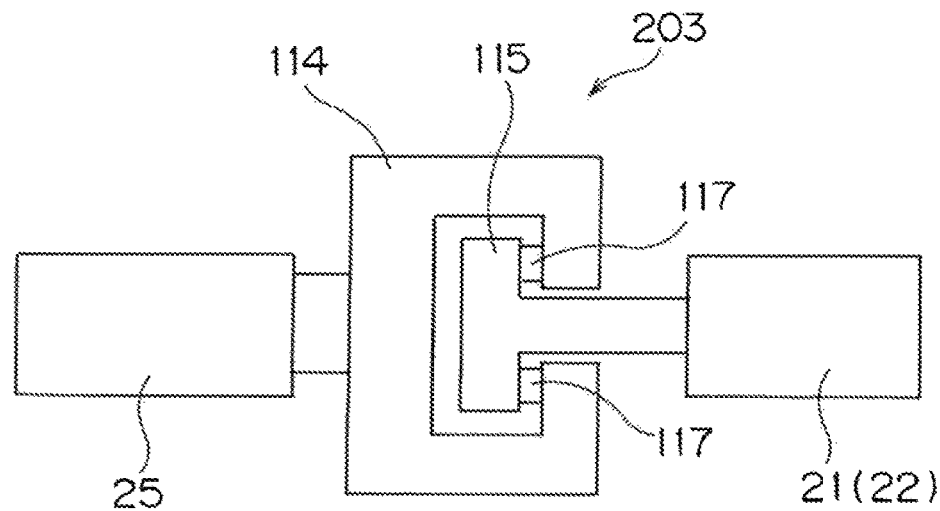
FIG. 10 is a schematic diagram of a pretension mechanism 203 according to a fourth embodiment.

FIG. 10 is a schematic diagram of a pretension mechanism 203 according to a fourth embodiment. Note that in the diagram, a first slide member 21 or a second slide member 22 and a chuck 25 are directly connected to each other by the pretension mechanism 203; however, when disposing a load cell 27, the load cell 27 is disposed between the first slide member 21 or the second slide member 22 and the pretension mechanism 203 or between the chuck 25 and the pretension mechanism 203.

The pretension mechanism 203 is configured to employ wedges 117 in place of the screws 116 in the third embodiment illustrated in FIG. 9. In the pretension mechanism 203 according to the fourth embodiment, by changing the size of the pair of wedges 117 to change the distance between a pin 25 and the chuck 25 connected to the first slide member 21 or the second slide member 22, pretension can be applied to a test piece 100.

Figure 11:
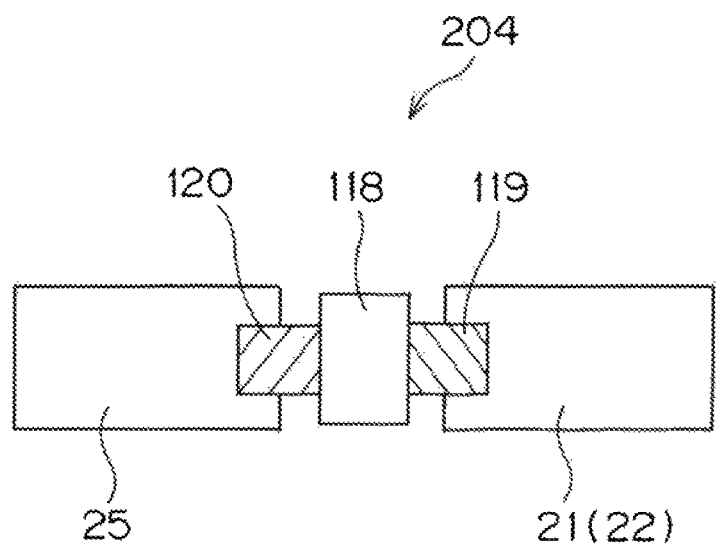
FIG. 11 is a schematic diagram of a pretension mechanism 204 according to a fifth embodiment.

FIG. 11 is a schematic diagram of a pretension mechanism 204 according to a fifth embodiment. Note that in the diagram, a first slide member 21 or a second slide member 22 and a chuck 25 are directly connected to each other by the pretension mechanism 204; however, when disposing a load cell 27, the load cell 27 is disposed between the first slide member 21 or the second slide member 22 and the pretension mechanism 204 or between the chuck 25 and the pretension mechanism 204.

The pretension mechanism 204 is configured to, between the first slide member 21 or the second slide member 22 and the chuck 25, dispose a compound screw member 118 of which both ends are formed with screw parts 119 and 120 facing in mutually opposite directions. The one screw part 119 of the compound screw member 118 is screwed into the first slide member 21 or the second slide member 22, and the other screw part 120 is screwed into the chuck 25. In the pretension mechanism 204, by rotating the compound screw member 118 around its axis to change the distance between a pin 25 and the chuck 25 connected to the first slide member 21 or the second slide member 22, pretension can be applied to a test piece 100.

Figure 12:
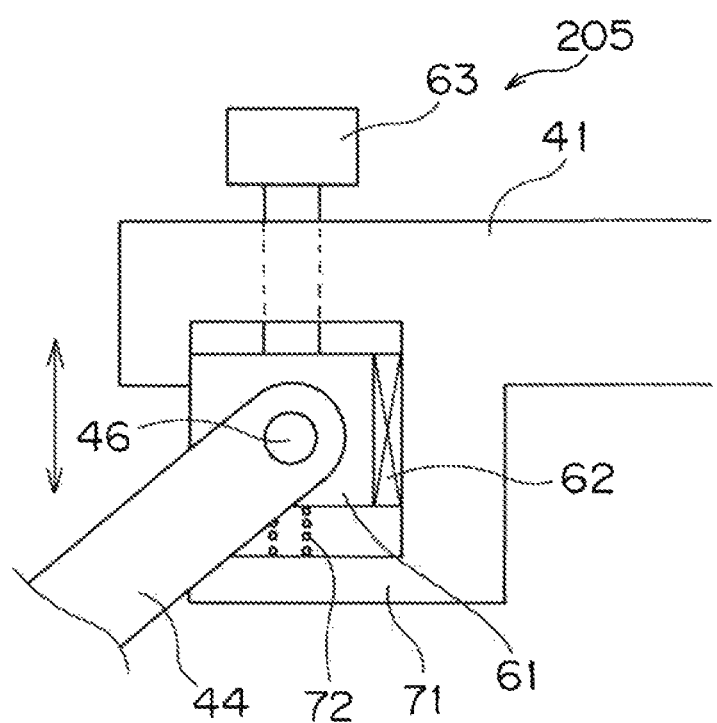
FIG. 12 is a schematic diagram of a pretension mechanism 205 according to a sixth embodiment.

FIG. 12 is a schematic diagram of a pretension mechanism 205 according to a sixth embodiment.

Any of the above-described first to fifth embodiments employs the configuration adapted to apply the pretension to the test piece 100 by changing the distance between the pin 45 and the chuck 24. On the other hand, the pretension mechanism 205 according to the sixth embodiment employs a configuration adapted to apply pretension to a test piece 100 by changing the position of a swing shaft 46 serving as the swing center of a link member 44.

That is, in the pretension mechanism 205, the swing shaft 46 is pivotally supported by a bearing member 61. The bearing member 61 is supported by a slide member 62 movably in a vertical direction with respect to a support part 41. Also, between the bearing member 61 and a flange part 71 of the support part 41, a spring 72 is disposed. In addition, in the support part 41, a screw 63 for pressing the bearing member 61 is disposed. In the pretension mechanism 205, by rotating the screw 63 to move the bearing member 61 together with the swing shaft 46 downward, the pretension can be applied to the test piece 100. Note that the above-described spring 72 is not necessarily required. Also, in FIG. 12, it may be configured to apply the pretension using a wedge that is disposed between the support part 41 and the bearing member 61 in place of the screw 63.

Figure 13:
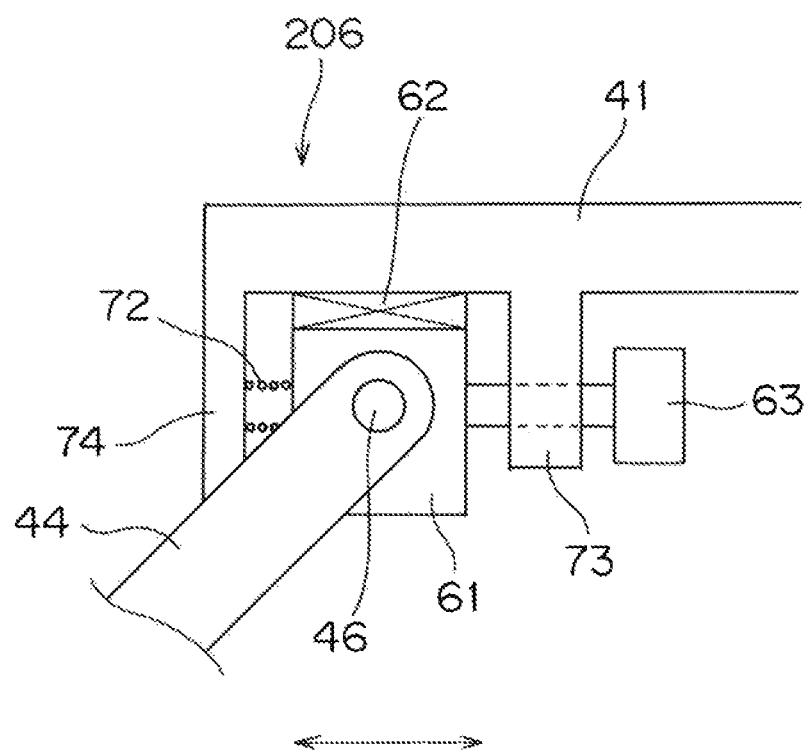
FIG. 13 is a schematic diagram of a pretension mechanism 206 according to a seventh embodiment.

FIG. 13 is a schematic diagram of a pretension mechanism 206 according to a seventh embodiment.

As with the pretension mechanism 205 according to the sixth embodiment illustrated in FIG. 12, the pretension mechanism 206 according to the seventh embodiment also employs a configuration adapted to apply pretension to a test piece 100 by changing the position of a swing shaft 46 serving as the swing center of a link member 44.

That is, in the pretension mechanism 206 as well, the swing shaft 46 is pivotally supported by a bearing member 61. The bearing member 61 is supported by a slide member 62 movably in a horizontal direction with respect to a support part 41. Also, between the bearing member 61 and a flange part 74 of the support part 41, a spring 72 is disposed. In addition, in a hanging part 73 of the support part 41, a screw 63 for pressing the bearing member 61 is disposed. In the pretension mechanism 206, by rotating the screw 63 to move the bearing member 61 together with the swing shaft 46 laterally, the pretension can be applied to the test piece 100. Note that the above-described spring 72 is not necessarily required. Also, in FIG. 13, it may be configured to apply the pretension using a wedge that is disposed between the support part 41 and the bearing member 61 in place of the screw 63.

Figure 14:
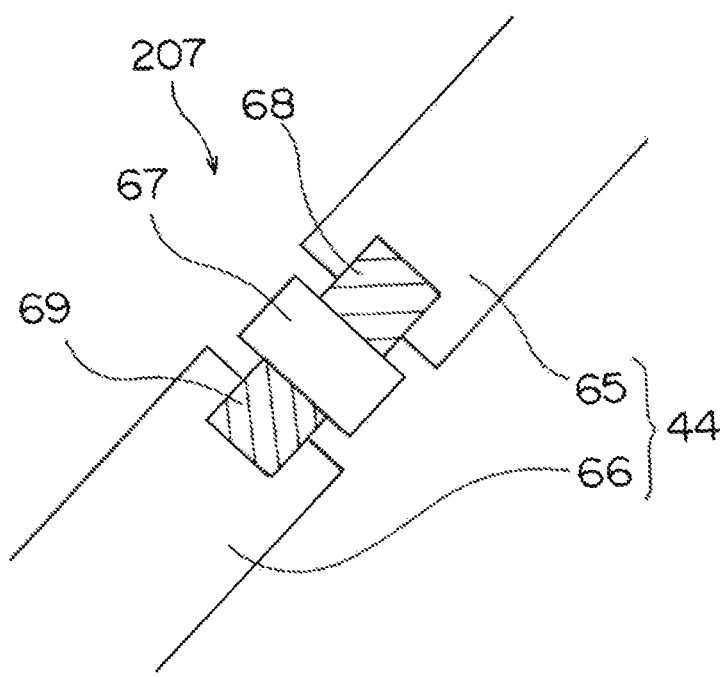
FIG. 14 is a schematic diagram of a pretension mechanism 207 according to an eighth embodiment.
Figure 15:
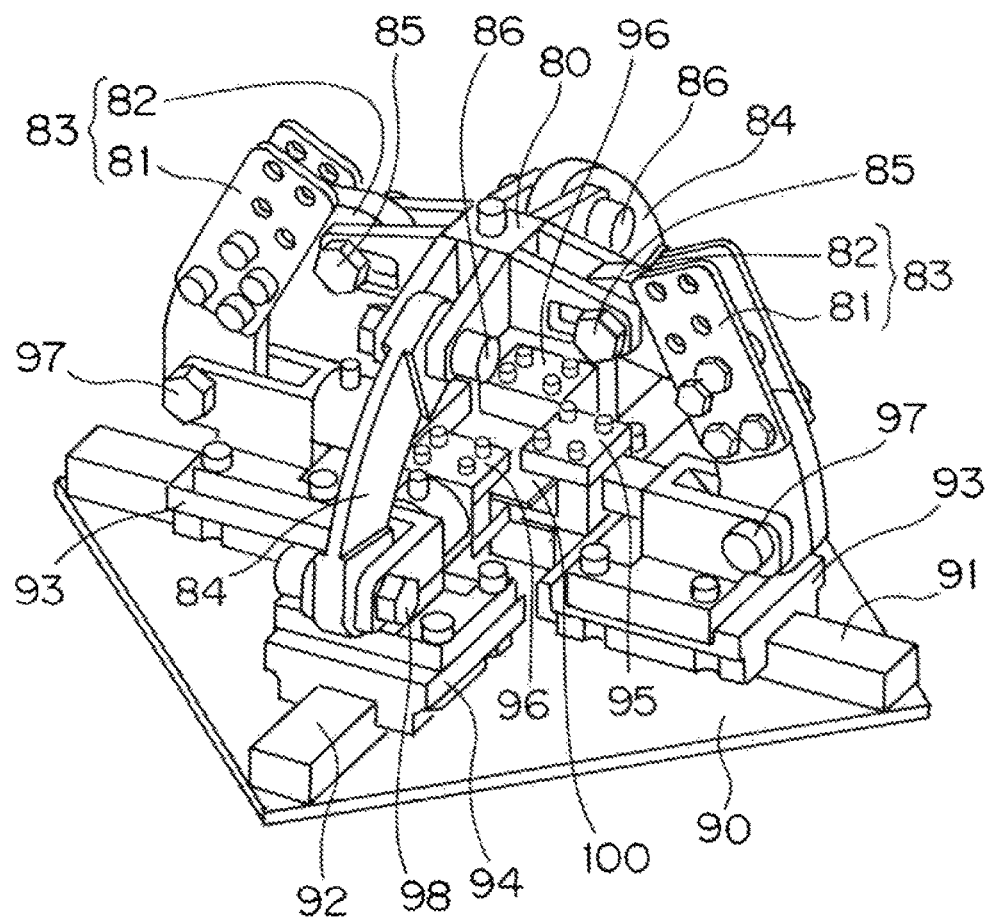
FIG. 15 is a perspective view illustrating a biaxial tension mechanism for applying test forces to a test piece 100 in a conventional material testing machine.

FIG. 14 is a schematic diagram of a pretension mechanism 207 according to an eighth embodiment.

Differently from the above-described first to seventh embodiments, the pretension mechanism 207 according to the eighth embodiment employs a configuration adapted to apply pretension to a test piece 100 by changing the length of a link member 44.

In the pretension mechanism 207, the link member 44 is configured to include a pair of link pieces 65 and 66. Also, the pretension mechanism 207 is configured to, between the link piece 65 and the link piece 66, dispose a compound screw member 67 of which both ends are correspondingly formed with screw parts 68 and 69 facing in mutually opposite directions. The one screw part 68 of the compound screw member 67 is screwed into the link piece 65, and the other screw part 69 is screwed into the link piece 66. In the pretension mechanism 207, by rotating the compound screw member 67 around its axis, the distance between the link piece 65 and the link piece 66 is changed to change the length of the link member 44. Using such an action, the pretension can be applied to the test piece 100 by rotating the compound screw member 67 in a direction to increase the distance between the link piece 65 and the link piece 66.

Note that in any of the above-described embodiments, described is the case of performing the biaxial tensile test adapted to use the first rail 23 and the second rail 24, which are disposed on the surface of the base part 26 in the mutually orthogonal directions, to move the pair of first slide members 21 and the pair of second slide members 22 in the mutually orthogonal directions, and thereby apply the tensile forces in the orthogonal directions to the test piece 100; however, the present invention may be applied to a material testing machine that performs a triaxial tensile test adapted to apply tensile forces in three axial directions to a test piece 100 by arranging a first rail 23 and a second rail 24 in intersecting directions, further arranging a third rail in a direction intersecting with the first and second rails 23 and 24, and sliding a third slide member connected to a chuck along the third rail. In addition, the present invention can also be applied to perform a material test adapted to apply tensile forces in four or more axial directions to the test piece 100.

REFERENCE SIGNS LIST

1 Biaxial tension mechanism
2 Upper unit
3 Lower unit
11 Base
12 Screw rod
13 Crosshead
16 Motor
21 First slide member
22 Second slide member
23 First rail
24 Second rail
25 Chuck
26 Base part
27 Load cell
29 Seating surface
31 Seat member
32 Seat member
33 Seat member
34 Pin 39 Screw
41 Support part
44 Link member
45 Pin
46 Swing shaft
47 Joint part
48 Convex part
61 Bearing member
62 Slide member
63 Screw
65 Link piece
66 Link piece
67 Compound screw member
100 Test piece
111 Connecting member
112 Connecting member
113 Screw
114 Connecting member
115 Connecting member
116 Screw
117 Wedge
118 Compound screw member
201 Pretension mechanism
202 Pretension mechanism
203 Pretension mechanism
204 Pretension mechanism
205 Pretension mechanism
206 Pretension mechanism
207 Pretension mechanism

The invention claimed is:

1. A material testing machine comprising:
  a pair of first moving members capable of moving in mutually approaching and separating directions along a first axis by being guided along a guide member;
  chucks correspondingly connected to the first moving members;
  a pair of second moving members capable of moving in mutually approaching and separating directions along a second axis intersecting with the first axis by being guided along a guide member;
  chucks correspondingly connected to the second moving members:
  a load member to be applied with a load by a load mechanism;
  four link members that are disposed in states of being swingable with respect to the load member correspondingly around swing shafts disposed in the load member; and
  connecting mechanisms adapted to connect end parts of the link members on sides opposite to the swing shafts to the first moving members and the second moving members correspondingly,
  the material testing machine transmitting the load applied to the load member to the pair of first moving members and the pair of second moving members through the four link members correspondingly, and thereby synchronously moving the pair of first moving members in the mutually separating directions along the first axis, as well as moving the pair of second moving members in the mutually separating directions along the second axis,
  the material testing machine comprising pretension mechanisms adapted to apply pretensions to a test piece by in a state where no load is applied to the load member by the load mechanism, moving the pair of chucks correspondingly connected to the pair of first moving member in the mutually separating directions along the first axis as well as moving the pair of chucks correspondingly connected to the pair of second moving members in the mutually separating directions along the second axis.

2. The material testing machine according to claim 1, wherein
  the pretension mechanisms change distances between the end parts of the link members on the sides opposite to the swing shafts and the chucks, and thereby apply the pretensions to the test piece correspondingly.

3. The material testing machine according to claim 2, wherein:
  the connecting mechanisms include pins and seating surfaces touching the pins correspondingly; and
  the pretension mechanisms apply the pretensions to the test piece by changing distances between the pins and the chucks correspondingly.

4. The material testing machine according to claim 3, wherein:
  the first moving members and the second moving members are configured to include seat members formed with the seating surfaces and slide members holding the seat members correspondingly; and
  the pretension mechanisms have pressing members that move the seat members with respect to the slide members correspondingly.

5. The material testing machine according to claim 1, wherein
  the pretension mechanisms apply the pretensions to the test piece by changing positions of the swing shafts correspondingly.

6. The material testing machine according to claim 5, wherein:
  the swing shafts are pivotally supported by bearing members movable in directions intersecting with longer directions of the link members correspondingly; and
  the pretension mechanisms comprise pressing members for pressing the bearing members, and apply the pretensions to the test piece by making the pressing members move the bearing members in the directions intersecting with the longer directions of the link members correspondingly.

7. The material testing machine according to claim 1, wherein
  the pretension mechanisms apply the pretensions to the test piece by changing lengths of the link members correspondingly.

8. The material testing machine according to claim 7, wherein:
  the link members correspondingly comprise pairs of link pieces connected through compound screw members each having both ends that are formed with screw parts facing in mutually opposite directions; and
  the pretension mechanisms apply the pretensions to the test piece by rotating the compound screw members to change distances between the pairs of link pieces correspondingly.

* * * * *